(12) United States Patent
Sato

(10) Patent No.: US 9,598,197 B2
(45) Date of Patent: Mar. 21, 2017

(54) DOUBLE-DECKER TUBE DISPENSER

(71) Applicant: TECHNOMEDICA CO., LTD., Yokohama-shi (JP)

(72) Inventor: Mitsuru Sato, Sendai (JP)

(73) Assignee: TECHNOMEDICA CO., LTD., Yokohama-Shi, Kanagawa (JP)

(*) Notice: Subject to any disclaimer, the term of this patent is extended or adjusted under 35 U.S.C. 154(b) by 1 day.

(21) Appl. No.: 14/413,683

(22) PCT Filed: Jul. 9, 2013

(86) PCT No.: PCT/JP2013/068787
§ 371 (c)(1),
(2) Date: Jan. 8, 2015

(87) PCT Pub. No.: WO2014/010608
PCT Pub. Date: Jan. 16, 2014

(65) Prior Publication Data
US 2015/0197362 A1    Jul. 16, 2015

(30) Foreign Application Priority Data
Jul. 10, 2012   (JP) ................................. 2012-154575

(51) Int. Cl.
*B65C 11/02*   (2006.01)
*B65C 9/02*    (2006.01)
(Continued)

(52) U.S. Cl.
CPC ................. *B65C 3/10* (2013.01); *B65C 9/02* (2013.01); *B65C 9/1865* (2013.01); *B65C 9/30* (2013.01);
(Continued)

(58) Field of Classification Search
USPC ..... 156/384, 387, 537, 538, DIG. 5, DIG. 6, 156/DIG. 8, DIG. 9, DIG. 49
See application file for complete search history.

(56) References Cited

U.S. PATENT DOCUMENTS

2011/0145006 A1* 6/2011 Pedrazzini ............ G06F 19/366
  705/2
2011/0173927 A1* 7/2011 Yamada ................. G01N 35/04
  53/236

FOREIGN PATENT DOCUMENTS

| JP | 08324527 A | * 12/1996 | ............... B65C 3/02 |
| JP | 2002-102210 A | 4/2002 | |
| JP | 2002-340910 A | 11/2002 | |

OTHER PUBLICATIONS

English Abstract of JP 08-324527 (May 15, 2016).*
Machine Translation of JP 08-324527 (May 17, 2016).*

* cited by examiner

*Primary Examiner* — Sing P Chan
(74) *Attorney, Agent, or Firm* — Knobbe Martens Olson & Bear LLP

(57) ABSTRACT

Provided is a double-decker tube dispenser that is not only compact but also highly portable, can be set easily on a cart, a desk, and the like, is capable of responding immediately in case of emergency such as disaster, and enables blood sampling tubes of different types to be prepared in response to blood sampling instructions from doctors. A blood sampling tube stocker device is arranged in an overlapping manner above a printing-and-pasting device, and hence a horizontal width can be extremely reduced. With this, the double-decker tube dispenser, which is not only significantly compact but also highly portable, and applicable not only to medium and small hospitals and hospital wards for inpatients, but also, for example, to facilities specializing in (Continued)

blood sampling, and enables use beside a sickbed, desktop use, and use on a mobile cart and the like in a state in which the dispenser is simply mounted thereon, is provided. The double-decker tube dispenser is capable of responding immediately in case of emergency such as disaster, and hence blood sampling tubes of different types can be prepared by being dispensed reliably one by one in response to blood sampling instructions from doctors.

6 Claims, 9 Drawing Sheets

(51) Int. Cl.
*B65C 9/04* (2006.01)
*B65C 9/46* (2006.01)
*B29C 65/48* (2006.01)
*B32B 37/12* (2006.01)
*B32B 37/26* (2006.01)
*B32B 38/10* (2006.01)
*B32B 38/14* (2006.01)
*B32B 39/00* (2006.01)
*B65C 3/10* (2006.01)
*G01N 35/04* (2006.01)
*B65C 9/18* (2006.01)
*B65C 9/30* (2006.01)
*B65C 9/40* (2006.01)
*G01N 35/00* (2006.01)

(52) U.S. Cl.
CPC ............... *B65C 9/40* (2013.01); *G01N 35/04* (2013.01); *G01N 2035/00861* (2013.01); *G01N 2035/0406* (2013.01); *G01N 2035/0465* (2013.01)

DOUBLE-DECKER TUBE DISPENSER

CROSS-REFERENCE TO RELATED APPLICATIONS

This application is the U.S. National Phase under 35. U.S.C. §371 of International Application PCT/JP2013/068787, filed Jul. 9, 2013, which claims priority to Japanese Patent Application No. 2012-154575, filed Jul. 10, 2012. The disclosures of the above-described applications are hereby incorporated by reference in their entirety.

TECHNICAL FIELD

The present invention relates to an extremely compact desktop tube dispenser for work of preparing blood sampling tubes in advance for a blood sampling step prior to a blood test, and more particularly, to a double-decker desktop tube dispenser having a blood sampling tube stocker device arranged above a printing-and-pasting device.

BACKGROUND ART

In blood test departments of hospitals, clinics, and other medical institutions, blood sampling staff (such as nurses) sample and store blood of patients into blood sampling tubes, and transport the blood sampling tubes to the test department. For blood tests, blood sampling tubes of various types are prepared in accordance with items of the blood tests. Normally, tests of various types are carried out simultaneously for each patient. Thus, blood sampling tubes of a plurality of types are automatically prepared for each of the patients by a blood sampling tube preparation apparatus. In addition, it is a common practice that a large number of patients are treated in a blood sampling room, and labels each printed with a barcode containing information items of a patient, a blood test, and the like are pasted to the blood sampling tubes prepared by the blood sampling tube preparation apparatus.

Further, at the time of reception of blood sampling, blood sampling reception tickets each printed with a barcode indicating, for example, a receipt number are issued to the patients. At the time of blood sampling operation, contents of those labels or reception tickets are read by an optical device such as a barcode reader. In this way, the patients and their blood sampling tubes are prevented from being mistakenly switched with each other.

As a technology for automating such blood sampling work and assisting the blood sampling work, a technology as disclosed in Patent Literature 1 is known. In the technology disclosed in Patent Literature 1, a drive device for driving and rotating an endless belt in a vertical direction (perpendicular direction) is utilized. In this belt drive device, a belt width is set to be equal to or larger than a longitudinal dimension of blood sampling tubes. Caterpillar-like partition plates are provided so as to project in an outer diameter direction from a belt surface, and a compartment on the belt surface between each pair of the partition plate on a front side and the partition plate on a rear side is used as a single blood sampling tube receiving portion (stock portion). In this way, a large number of the blood sampling tube receiving portions are formed on a single belt surface. In this case, a single belt drive device is configured to receive blood sampling tubes of the same type. Further, stocker mechanisms that utilize belt drive devices for receiving blood sampling tubes with such a caterpillar configuration are arranged so as to overlap with each other in a plurality of stages in upper and lower directions. With this, blood sampling tubes of a plurality of types can be handled.

Based on blood sampling ordering information from doctors, blood sampling tubes that are necessary for sampling blood of patients are taken out from corresponding blood sampling stocker mechanism portions. Using label printing-and-pasting means, information items of blood sampling from the patients are printed onto labels, and the printed labels are pasted to the taken-out blood sampling tubes. Then, the blood sampling tubes for each patient, to which the labels are pasted, are transported by delivery means to a blood sampling tube collection portion, and are received into a tray in the blood sampling tube collection portion.

In such a blood sampling tube preparation apparatus, the stocker mechanism portions are arranged so as to vertically overlap with each other. Thus, a dimension in a height direction is considerably large, which causes a problem of an increase in size of the apparatus itself. In addition, in order to handle the blood sampling tubes of the plurality of types, there is no other way than to expand respective caterpillars in a horizontal direction. As a result, a horizontal width of the entire apparatus becomes significantly larger, which causes a problem of a difficultly in employment in medical institutions due to space limitations.

Meanwhile, as a method of solving the related-art problems described above, a technology of the blood sampling tube preparation apparatus is known as disclosed in Patent Literature 2. In the technology disclosed in Patent Literature 2, which is previously filed by the inventors of the present invention, a test tube holding member is arranged along and on an inside of reciprocating belts of a single conveyor belt so that a lower end surface of a cap of each test tube is supported with the test tube holding member and an upper end surface of the forward feeding belt. In addition, the test tubes are fed by the forward feeding belt through intermediation of the caps. Using such a stocker, test tubes of a single type can be conveyed with a test tube conveying apparatus of a single type, and hence the number of conveying apparatus can be suppressed to the requisite minimum. Further, a width of each of the stockers is only several centimeters, and hence there is an advantage in that, even in a case where stockers of a plurality of types are arrayed correspondingly to test tubes of various types, an overall width dimension can be set significantly smaller than those in the related art.

CITATION LIST

Patent Literature

[PTL 1] JP 2005-67660 A
[PTL 2] JP 4356096 B

SUMMARY OF INVENTION

Technical Problems

However, in the technology disclosed in Patent Literature 2, a driving force for the conveyor belt is transmitted to the lower end surface of each of the blood sampling tube caps, which is placed on the upper end surface of the forward feeding belt, through intermediation of the upper end surface of the forward feeding belt. Meanwhile, another side of the lower end surface of each of the blood sampling tube caps is moved while sliding on the support rail. Thus, when frictional resistance between the support rail and the cap lower end surface is high, the frictional resistance exceeds the driving force for conveying the blood sampling tubes, which is transmitted from the upper end surface of the forward feeding belt to the lower end surface of each of the blood sampling tube caps. As a result, the lower end surface of each of the blood sampling tube caps and the upper end surface of the conveying belt slip relative to each other, which causes a problem in that the blood sampling tubes cannot be conveyed. The rubber-capped blood sampling tubes having a high friction coefficient conspicuously cause this problem, that is, a problem in that conveyance cannot be performed at all.

Further, in the above-mentioned related-art technology disclosed in Patent Literature 2, the lower end surface of the blood sampling tube cap is supported by the support rail on one side, and supported by the upper end surface of the conveyor belt on another side so that feeding by the conveyor belt is directly transmitted through abutment of the conveyor belt against the cap lower end surface. Thus, there is a problem in durability, which may be caused by abrasion due to contact between the cap lower end surface and the end surface of the conveyor belt. In addition, there is a risk in that the conveyor belt is twisted to draw the caps of the blood sampling tubes into between the belts, which causes the blood sampling tubes to fall.

Still further, there is another problem in that sticker caps having outer diameter dimensions slightly larger than outer diameter dimensions of the blood sampling tubes cannot be employed. This is because a width dimension necessary for placing the lower end surface of the cap on the end surface of the conveyor belt cannot be secured. In this way, in the stocker configuration of supporting the lower end surfaces of the caps of the blood sampling tubes, conveyance itself of blood sampling tubes with caps having insufficient sizes cannot be performed. In particular, a large number of foreign blood sampling tubes are this type of blood sampling tubes, and hence there is a serious problem in that types of usable blood sampling tubes are significantly limited.

In addition, there is another serious problem in that blood sampling tubes without caps cannot be utilized at all.

Yet further, in the technology disclosed in Patent Literature 2, a horizontal width dimension of the entire apparatus can be reduced in comparison with that in the technology disclosed in Patent Literature 1, but a horizontal width dimension that is equal to a sum of a width dimension of the stocker device and a width dimension of the printing-and-pasting device is still needed. In this way, there is still room for improvement on application to desktop use.

In view of the above-mentioned circumstances, the inventors of the present invention provide an apparatus that is improved to overcome the related-art problems described above. A double-deck structure in which a blood sampling tube stocker device is arranged in an overlapping manner above a printing-and-pasting device is employed, and hence a horizontal width can be extremely reduced. With this, there is provided a double-decker tube dispenser that is not only significantly compact but also highly portable, and applicable not only to medium and small hospitals and hospital wards for inpatients, but also, for example, to facilities specializing in blood sampling, and enables use beside a sickbed, desktop use, and use on a mobile cart and the like in a state in which the dispenser is simply mounted thereon. The double-decker tube dispenser is capable of responding immediately in case of emergency such as disaster, and hence blood sampling tubes of different types can be prepared by being dispensed reliably one by one in response to blood sampling instructions from doctors.

Solution to Problems

According to a measure of claim 1, which is employed in one embodiment of the present invention to solve the problems described above, there is provided a double-decker tube dispenser, including: a blood sampling tube stocker device including a plurality of independent blood sampling tube stockers arranged in a vertical column and in a horizontal row, for receiving blood sampling tubes of corresponding types in a horizontal posture, respectively; first conveying means for dispensed blood sampling tubes, which is arranged below units of the plurality of independent blood sampling tube stockers in the vertical column, for conveying the blood sampling tubes dispensed from the plurality of independent blood sampling tube stockers to a near side; second conveying means arranged on a terminal end side of the first conveying means in a direction orthogonal to the first conveying means, for receiving the blood sampling tubes conveyed by the first conveying means, and transporting the received blood sampling tubes up to a position corresponding to blood sampling tube transfer means provided on a transportation path of the second conveying means; the blood sampling tube transfer means for pushing out the blood sampling tubes on the second conveying means in a direction orthogonal to the transportation direction of the transportation means; and a label printing-and-pasting device arranged in proximity to the blood sampling tube transfer means, in which the label printing-and-pasting device is positioned below the units of the plurality of independent blood sampling tube stockers in the vertical column corresponding to blood sampling tube supply means.

According to a measure of claim 2, which is employed in one embodiment of the present invention to solve the problems described above, the double-decker tube dispenser according to claim 1 further includes: orientation detection means for blood sampling tubes, which is arranged on one end side of the second conveying means; and arrival detection means arranged on another end side of the second conveying means. The blood sampling tube transfer means is arranged on the another end side of the second conveying means.

According to a measure of claim 3, which is employed in one embodiment of the present invention to solve the problems described above, the double-decker tube dispenser according to claim 1 or 2 further includes blood sampling tube delivery means arranged below and parallel to the second conveying means.

According to a measure of claim 4, which is employed in one embodiment of the present invention to solve the problems described above, the double-decker tube dispenser according to any one of claims 1 to 3 further includes a printing device arranged below one of the units of the plurality of independent blood sampling tube stockers in the vertical column, for printing labels to be manually pasted. The label printing-and-pasting device according to claim 1 is arranged below another of the units of the plurality of independent blood sampling tube stockers in the vertical column.

According to a measure of claim 5, which is employed in one embodiment of the present invention to solve the problems described above, the double-decker tube dispenser according to any one of claims 1 to 4 further includes an intermediate conveyor provided between at least one of the first conveying means for dispensed blood sampling tubes, which is arranged below the units of the plurality of independent blood sampling tube stockers in the vertical column, and the second conveying means. The blood sampling tubes conveyed by the first conveying means are fed to the second conveying means through intermediation of the intermediate conveyor.

According to a measure of claim 6, which is employed in one embodiment of the present invention to solve the problems described above, in the double-decker tube dispenser according to any one of claims 1 to 5, the units of the plurality of independent blood sampling tube stockers in the vertical column include two units of the plurality of independent blood sampling tube stockers in the vertical column, which are arranged in a horizontal direction, and a width dimension of an entire apparatus is set to be larger than a total width dimension of the plurality of independent blood sampling tube stockers in the horizontal direction by an amount corresponding to a dimension of a casing.

Advantageous Effects of Invention

According to the invention of claim 1, the label printing-and-pasting device can be arranged below the blood sampling tube stocker device in which the units of the plurality of blood sampling tube stockers in the vertical column are arranged in the horizontal row, that is, has double-decker structure. Thus, in particular, a horizontal width dimension of the tube dispenser can be further reduced by an amount corresponding to a horizontal width dimension of a printing-and-pasting dimension in comparison with the related art (Patent Literature 2). Thus, a compact apparatus can be provided. Further, the blood sampling tubes dispensed from the blood sampling tube stockers are transported to the near side by the first conveying means, and then transported by the single second conveying means to the front of the printing-and-pasting device. In this way, a structure of means for transporting the blood sampling tubes can be simplified.

Further, in the blood sampling tube stockers of the apparatus of the present invention, the blood sampling tubes are received in a horizontal posture (laid posture). In comparison with the related art (Patent Literature 2) of the cap support type, a problem in that the blood sampling tubes cannot be conveyed due to fall and slippage of the blood sampling tubes does not occur.

According to the invention of claim 2, orientations of the blood sampling tubes can be detected by the orientation detection means, and a direction of printing to the labels can be printed in any of forward and reverse directions in accordance with the orientations. Thus, the labels can be pasted in a proper direction to the blood sampling tubes. With this, the blood sampling tubes can be randomly loaded regardless of their orientations into the blood sampling tube stockers, and hence operation of replenishing the blood sampling tubes into the blood sampling tube stockers can be facilitated.

Further, arrival of the blood sampling tubes can be detected by the arrival detection means. Thus, in response to a signal therefrom, the blood sampling tube transfer means is driven. With this, the blood sampling tubes that have arrived thereat can be transferred to the printing-and-pasting device.

According to the invention of claim 3, the blood sampling tubes, to which the labels are pasted, can be delivered by being conveyed from the printing-and-pasting device side to another side.

According to the invention of claim 4, the printing device for labels to be manually pasted is arranged below the one of the units of the plurality of blood sampling tube stockers in the vertical column, and the label printing-and-pasting device is arranged below the another of the units of the plurality of blood sampling tube stockers in the vertical column. Thus, normally, the blood sampling tubes can be prepared by printing patient information and the like to the labels by the printing-and-pasting device, and pasting the labels to the blood sampling tubes. Further, as for particular blood sampling tubes that are not arranged in any of the blood sampling tube stockers, only patient information is printed to the labels by the printing device for manual pasting, and the labels are manually pasted by a hospital staff who prepared the particular blood sampling tubes.

According to the invention of claim 5, the intermediate conveyor is provided between the at least one of the first conveying means for dispensed blood sampling tubes and the second conveying means. The blood sampling tubes that are dispensed from the blood sampling tube stockers are conveyed to the near side by the first conveying means. In the example of the figure, the blood sampling tubes, which are dispensed from the unit of the blood sampling tube stockers on the left side, fall directly onto the second conveying means. Meanwhile, the blood sampling tubes, which are dispensed from the unit of the blood sampling tube stockers on the right side, are once transferred onto the intermediate conveyor. Then, those blood sampling tubes are conveyed to the left side in FIGS. 2 and 5 by the intermediate conveyor, and dropped and supplied from a terminal end side onto the second conveying means therebelow.

According to the invention of claim 6, the two blood sampling tube stockers are provided in the horizontal direction. When the two blood sampling tube stockers provided in the horizontal direction are employed, the horizontal width dimension of the entire apparatus can be set to 350 mm.

DESCRIPTION OF EMBODIMENTS

Figure 1:
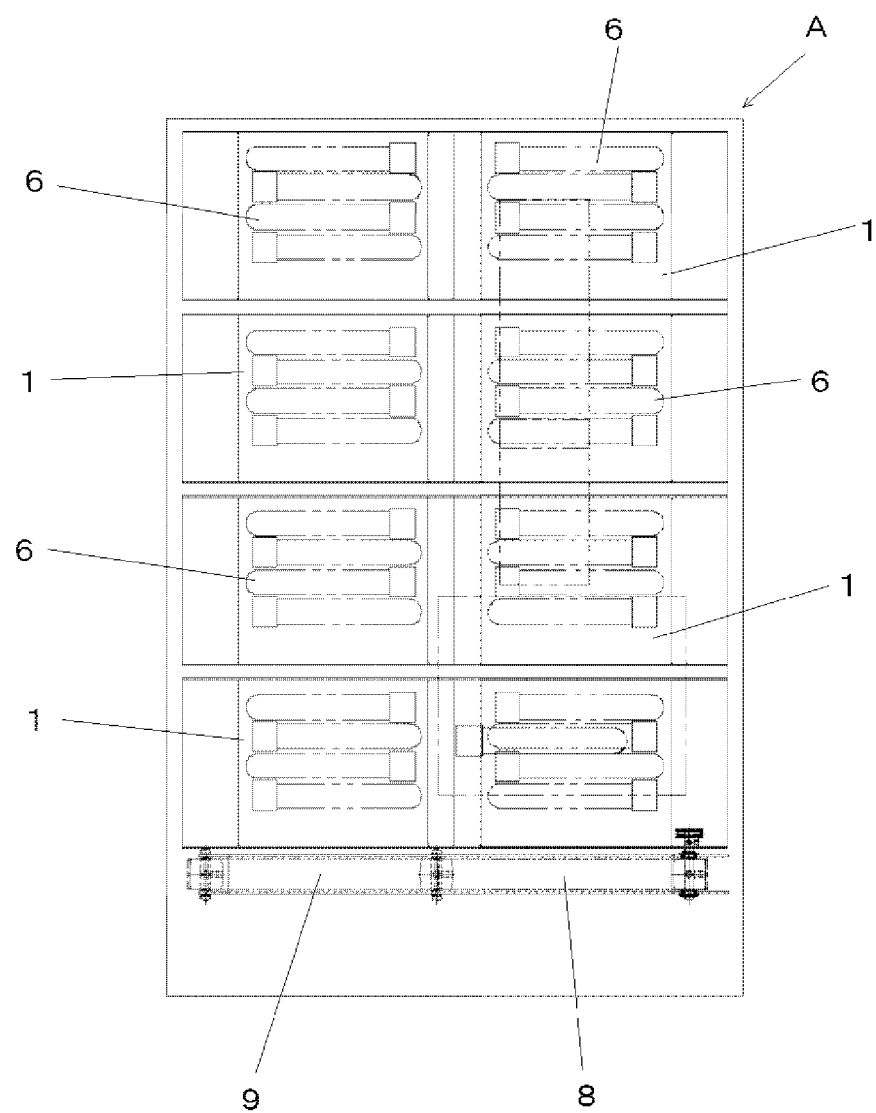
FIG. 1 is an overall plan view of a tube dispenser according to an embodiment of the present invention.

Now, description is made of configurations of the present invention with reference to embodiments of the invention, which are illustrated in the drawings. First, description is made of a layout of devices and mechanisms of a double-decker tube dispenser with reference to FIGS. 1 to 3.

As illustrated in the plan view of FIG. 1, in this tube dispenser A, a total of eight blood sampling tube stockers 1 are arrayed, specifically, four in vertical columns and two in horizontal rows. Those stocker devices, that is, the eight stockers 1 integrally turn upward from a near side about a lower end surface side of two innermost stockers in the horizontal row so that an entire stocker unit can be opened. With this, replacement, repair, and the like of a stocker main body 2, a dispensing roll 3, an auxiliary roll 4 for supporting and ensuring dispensing operation, and a drive motor 5 for those rolls, which construct each of the stockers 1, can be easily performed.

In addition, below each of the stockers 1 in the vertical columns, there is provided first conveying means 7 of a conveyor type with partition plates for dispensed blood sampling tubes (hereinafter referred to as "conveyor-type first conveying means" or simply as "first conveying means") for conveying blood sampling tubes 6 dispensed from the stockers 1. In this embodiment, two stockers 1 are provided in the horizontal rows, and hence two conveyor-type first conveying means 7 are set as illustrated in the front view of FIG. 2. With this, the blood sampling tubes 1 dispensed from the blood sampling tube stockers 1 in the vertical columns can be respectively received by the two conveyors 7.

Figure 2:
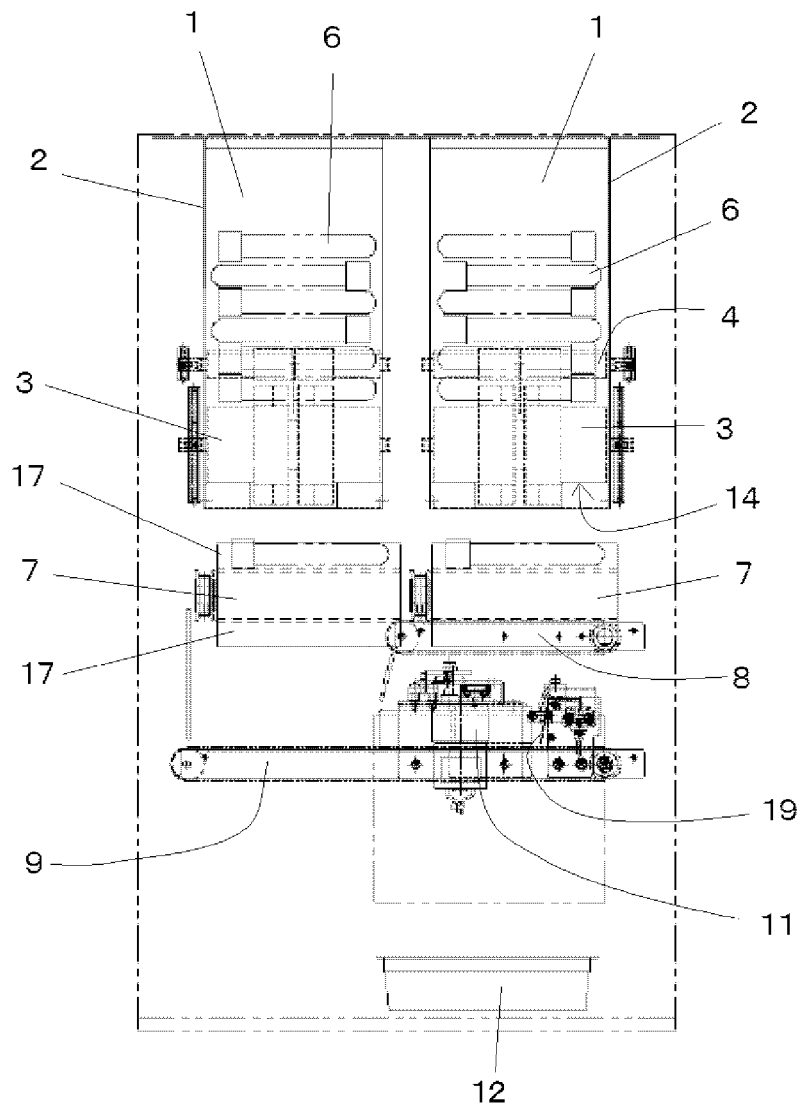
FIG. 2 is an overall front view of the tube dispenser according to the embodiment of the present invention.

Of the two conveyor-type first conveying means 7, on a terminal end side (left side in FIG. 3) of the first conveying means 7 positioned on the right side in FIG. 2, an intermediate conveyor 8 extending from a right end side to a left end side of a unit of the blood sampling tube stockers on the right side is arranged in a direction orthogonal to the first conveying means 7. Meanwhile, nothing is set on a terminal end side of the conveyor-type first conveying means 7 positioned on the left side in FIG. 2, and a space in which the blood sampling tubes 6 fall by their own weight is secured.

Further, below the intermediate conveyor 8, second conveying means 9 for the blood sampling tubes is arranged in parallel thereto. The second conveying means 9 is arranged so as to cover the two first conveying means 7 in a range of from a left end side to the right end side. On a terminal end side of the second conveying means 9 (right side in FIG. 2), there is provided a slider (blood sampling tube transfer means) 11 for pushing out and supplying the blood sampling tubes 6 having arrived thereat to printing-and-pasting means 10.

In this way, directly below the intermediate conveyor 8, the terminal end side of the second conveying means 9 for the blood sampling tubes, the slider 11, and sensors such as an arrival sensor are arranged. Thus, the blood sampling tubes 6 cannot be dropped and supplied from the unit of the stockers on the right side directly to a part corresponding to the slider 11. Thus, the blood sampling tubes 6 dispensed from the unit of the stockers on the right side are once moved to the left side by the intermediate conveyor 8, and are dropped and supplied onto the supply conveyor 9 therebelow. In this way, those blood sampling tubes 6 are supplied to the slider 11 side.

Figure 3:
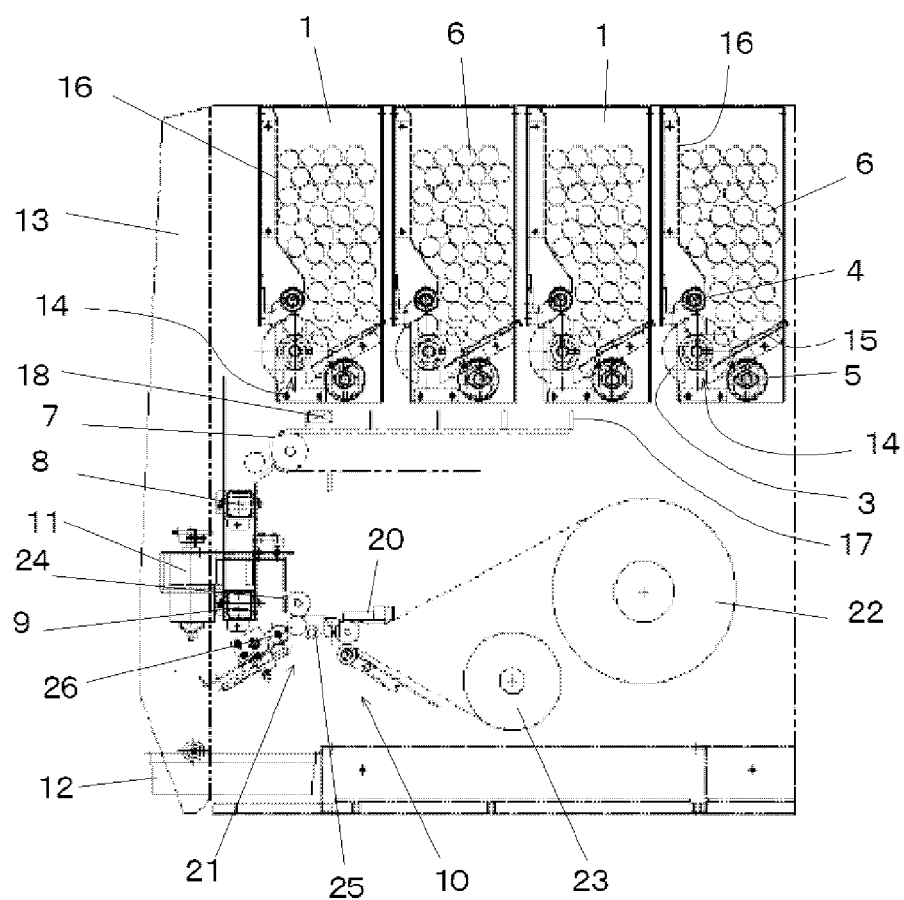
FIG. 3 is a right side view of mechanism portions of the tube dispenser according to the embodiment of the present invention.

Still further, as illustrated in the front view of FIG. 2 and the right side view of FIG. 3, a mounting portion for a tray 12 is provided on the near side with respect to the printing-and-pasting means 10. The blood sampling tubes for each patient, to which labels printed with information items of a patient, a blood test, and the like are pasted, are received in the tray 12 prepared thereat. In this tray mounting portion, an optical sensor (not shown) for detecting presence or absence of the tray 12 is arranged. The sensor may be sensors of a type in which light emitted from a light projecting sensor is detected by a light receiving sensor, and may be a light emitting-and-receiving sensor of a reflection type.

Yet further, on an upper surface of a front hatch 13 on the near side of an apparatus main body, there is provided a monitor (not shown) for displaying conditions of switches and mechanisms, such as a setting condition display unit.

In addition, on a rear surface side of the apparatus main body, a touch panel monitor (not shown) is mounted so as to be freely removable through intermediation of an arm having adjustable joints. This touch panel monitor doubles as an input unit and a monitor of a computer (CPU) built in an electronic device chamber below a unit of the stockers on the left side, and has a size of approximately 19 inches. This touch panel monitor displays, for example, an initial operation screen, a main screen, a detail status screen, a maintenance menu screen, and the like. In addition, using relay software installed in the CPU, communication conditions at the time of communication with a hospital information system (HIS) and a laboratory information system (LIS) of medical institutions such as a hospital, and patient information, blood sampling instruction information, and the like that are acquired from the systems such as the HIS and the LIS are displayed.

Yet further, on the rear surface side of the apparatus main body 2, as interfaces between the apparatus main body and the built-in computer, there are provided, for example, an insertion throttle for a radio board, a board for external connection devices, and the like, an R232C terminal, a voice input/output terminal, USB ports to be used for connection to a FAX and the like and connection to other external devices, a LAN connection port, and a plurality of power supply terminals adaptable to power sources of various types, such as foreign power supply terminals.

According to this tube dispenser A, the unit of the blood sampling tube stockers on the right side is positioned above the printing-and-pasting means 10. Meanwhile, below the unit of the blood sampling tube stockers on the left side, the electronic device chamber for installing therein a power supply unit, the CPU, an electronic substrate, and the like is formed. Thus, as best illustrated in the plan view of FIG. 1, a horizontal width dimension of the entire tube dispenser A is significantly small, that is, equal to a sum of horizontal width dimensions of the two blood sampling tube stockers 1 and 1 in the horizontal rows and a dimension of a casing. The small horizontal width dimension enables, irrespective of space limitation, application not only to medium and small hospitals and hospital wards for inpatients, but also, for example, to facilities specializing in blood sampling, and enables use beside a sickbed, desktop use, and use on a mobile cart and the like in a state in which the dispenser is simply mounted thereon. In addition, there is an advantage of immediate emergency response in case of disaster and the like, and hence blood sampling tubes of different types can be prepared by being dispensed reliably one by one in response to blood sampling instructions from doctors.

Next, description is made of each of the devices and mechanisms of the tube dispenser A. First, description is made of the blood sampling tube stocker 1 with reference to FIGS. 1 to 3. As illustrated in the plan view of FIG. 1, the blood sampling tube stocker 1 according to this embodiment includes a rectangular casing (stocker main body 2) formed by bending a thin metal plate such as a stainless plate, an aluminum alloy plate, and a steel plate. The stocker main body 2 has upper and lower opening planes. The upper opening plane serves as an inlet port for the blood sampling tubes 6, and the dispensing roll 3 is arranged in the lower opening plane. In an outer peripheral surface of the dispensing roll 3, recessed grooves 14 for receiving therein the dropped blood sampling tubes 6 are formed respectively at opposed positions. Further, an inclined bottom plate 15 configured to move upward and downward is interposed between the dispensing roll 3 and one of inner surfaces of the casing, and is designed so as to cause the blood sampling tubes 6 to be easily fitted into the recessed grooves 14 of the dispensing roll 3.

Further, the auxiliary roll 4, which has a small diameter, is arranged above the dispensing roll 3. The auxiliary roll 4 rotates in a direction reverse to that of the dispensing roll 3 so that, in a case where blood sampling tubes adhering to each other, such as rubber-capped blood sampling tubes, are to be collectively dispensed, the blood sampling tubes adhering to the blood sampling tube in the recessed groove 14 is pushed back to an opposite side and separated therefrom. In this way, the auxiliary roll 4 has a function to reliably dispense only the blood sampling tube fitted in the recessed groove 14. In a space below the inclined bottom plate 15, a motor 5 for driving the dispensing roll 3 and the auxiliary roll 4 and moving the inclined bottom plate 15 upward and downward is arranged.

Still further, above the auxiliary roll, there is provided a curved guide plate 16 for guiding the blood sampling tubes, which are loaded in the stocker main body, so that those blood sampling tubes are easily fitted into the recessed grooves 14 when coming closer to the dispensing roll 3. In addition, in the vicinity of the dispensing roll 3, an attachment to be pushed up by the blood sampling tubes 6 that are fitted in the recessed grooves 14 when the blood sampling tubes 6 come to a position directly thereabove is arranged. The attachment blocks an infrared signal and the like from an optical sensor, and issues a signal for causing the dispensing roll 3 to wait at the position directly thereabove.

The conveyor-type first conveying means 7 with partition plates, which is arranged below each of the units of the stockers in the vertical columns, includes partition plates 17 provided upright with respect to the conveyor at a predetermined interval. The blood sampling tubes 6 dispensed from the dispensing roll 3 of each of the stockers 1 are received in compartments between those partition plates 17, and conveyed in this state up to positions of the intermediate conveyor 8 and the blood sampling tube supply conveyor 9. On the terminal end side of the conveyor-type first conveying means 7, a sensor 18 for detecting presence or absence of the blood sampling tubes 6 is arranged so that subsequent blood sampling tubes 6 are prevented from being supplied to the printing-and-pasting means 10 side before operation of printing and pasting is completed.

Note that, in order that the blood sampling tubes 6, which are dispensed from the dispensing roll 3 of the blood sampling tube stocker 1 on the near side in each of the vertical columns near the intermediate conveyor 8 and the second conveying means 9, are dropped and supplied directly to the intermediate conveyor 8 and the second conveying means 9, overall positions of those stockers 1 are arranged closer to a front surface side of the apparatus main body. With this, the blood sampling tube stockers 1 most on the near side can be drawn to the front surface side of the apparatus main body by an amount corresponding to approximately ½ of a depth dimension of the stocker 1. Thus, a depth dimension of the entire apparatus can be reduced. Further, the dispensing rolls 3 of the blood sampling tube stockers 1 most on the near side do not start dispensing operation until a label pasting completion signal is output from the printing-and-pasting device.

On the terminal end side of the second conveying means 9, an arrival detection plate 19 for the blood sampling tubes 6 is provided. The arrival detection plate 19, which waits in an obliquely inclined posture under a normal state as illustrated in FIG. 2, enters a perpendicularly downward state by being pressed by the blood sampling tubes 6 fed thereto, and simultaneously determines a stop position of the blood sampling tubes 6. Under the inclined waiting state, the arrival detection plate 19 blocks light emitted from a detection sensor (not shown) such as an infrared sensor and a photo sensor including a light emitting element and a light receiving element, and allows the light emitted from the light emitting element to be received by the light receiving element under the perpendicularly downward state at the time of arrival of the blood sampling tubes 6.

Further, as illustrated in FIGS. 2 and 3, in a side surface portion with respect to the stop position of the blood sampling tubes 6, the dispensing slider (blood sampling tube transfer means) 11 for the blood sampling tubes 6 is provided so as to reciprocate in a direction orthogonal to a conveying direction of the blood sampling tube supply conveyor 9. With this, the blood sampling tubes 6 on the conveyor 9 are pushed out and dropped and supplied to a pasting position of the label pasting device.

Note that, right in front of the arrival detection plate 19, orientation detection means for detecting orientations of the blood sampling tubes 6 is provided (not shown). The orientation detection means includes a light emitting element, and light emitted therefrom is blocked by caps of the blood sampling tubes in a case where the caps erroneously abut first against the arrival detection plate 19 and the blood sampling tubes stop. In this way, the orientations of the blood sampling tubes 6 can be detected. In response to the detection of the orientations of the blood sampling tubes 6, signals are output to a label printing device 20 so that a printing direction of labels is switched between forward and reverse in accordance with the orientations of the blood sampling tubes 6.

As illustrated in FIG. 3, a label pasting device 21 includes a supply roll 22 for labels pasted to a continuous release sheet, and a take-up roll 23 for taking up the release sheet. The labels and the release sheet paid out from the supply roll 22 are folded back at an acute angle and moved in this state. With this, only the labels, which are repulsive (higher in elasticity than the release sheet and difficult to fold), are released from the release sheet. The labels are fed straight as they are and supplied to the pasting device 21 side, and only the residual release sheet is taken up by the take-up roll 23. On an upstream side with respect to this releasing portion, a printing device 20 for printing patient information items and the like to the labels is arranged. The information items to be printed are acquired via the interfaces of the computer (CPU) built in a control unit of the tube dispenser, which are connected, for example, to a computer of a host medical system and the like or computer terminals of doctors, specifically, acquired from its database or their hard disks. Further, in a feed direction of the labels released from the release sheet, the pasting device 21 including a drive roller 24, a support roller 25, and a pressure roller 26 arranged in a freely advancing and retracting manner is arranged. In addition, obliquely below the pasting device 21, the mounting portion for the tray 12 is provided.

Next, description is made of an operating mode of the tube dispenser A structured as described above. First, through opening portions of the stockers 1, which are formed through an upper surface of the apparatus main body, the blood sampling tubes 6 of different types are respectively loaded in the stockers. Orientations of the blood sampling tubes 6 need not be uniform. Under such a state, a power switch of the apparatus main body is turned ON so that the CPU of the built-in computer is activated to operate control software. In this way, blood sampling information of patients to undergo blood sampling is acquired from computers of the host HIS and LIS and the like or the computer terminals of doctors. The information acquired from those hosts is displayed on the touch panel monitor (not shown).

Based on the information acquired as described above, the control unit determines which type of blood sampling tube is selected, and causes the drive motor 5 to drive the blood sampling tube stocker 1 in which the blood sampling tube 6 of the corresponding type is stocked, the dispensing roll 3 to rotate in a counterclockwise direction in FIG. 3, and the auxiliary roll 5 to rotate in a clockwise direction. By driving those rolls 3 and 4, the blood sampling tube 6 is fitted and received in the recessed groove 14 of the dispensing roll 3. At this time, even in a case where a cap of the blood sampling tube 6 fitted in the recessed groove 14 adheres to a cap of another blood sampling tube 6, the another blood sampling tube 6 is pushed back by the auxiliary roll 4, and perfectly separated from the blood sampling tube 7 in the recessed groove 14. Then, when the dispensing roll 3 further rotates in the counterclockwise direction, the recessed groove 14 is then directed downward, and the blood sampling tube 6 received therein is dropped by its own weight and supplied to a portion between the partition plates 17 of the transportation conveyor 7, which is provided below the dispensing roll 3. Then, the blood sampling tube 6 is conveyed by the transportation conveyor 7 to the left side in FIG. 3, and stops in abutment against a stopper. Simultaneously, supply of the blood sampling tube 6 can be detected by the sensor 18 on the terminal end side.

In a case where no blood sampling tubes wait at the part corresponding to the slider 11, the conveyor-type first conveying means 7 drops and supplies the blood sampling tube 6, which is detected on the terminal end side thereof by the sensor 18, onto the second conveying means 9 or the intermediate conveyor 8. In a case where the blood sampling tube waits at the part corresponding to the slider 11, the blood sampling tube 6 is held and caused to wait at this position. As illustrated in FIG. 2, the blood sampling tube 6, which is dropped and supplied onto the intermediate conveyor 8, is conveyed by the intermediate conveyor 8 to the left direction in FIG. 2, and then falls from a terminal end side thereof so as to be transferred onto the second conveying means 9 therebelow. At this time, depending on a level difference between the intermediate conveyor 8 and the second conveying means 9 therebelow, short-sized capped blood sampling tubes (for example, approximately 75 mm) fall from a cap side onto the second conveying means 9, and each rotate over half about a bottom thereof in a counterclockwise direction along with movement of the second conveying means 9. In this way, the short-sized capped blood sampling tubes are transferred onto the second conveying means 9. Further, long-sized blood sampling tubes (for example, approximately 105 mm) fall from the intermediate conveyor 8 onto the second conveying means 9 therebelow under a state in which almost all parts over an entire length of those blood sampling tubes are separated from the intermediate conveyor 8. Thus, the long-sized blood sampling tubes are transferred onto the second conveying means 9 in an original posture without rotating.

At this time, supply of the long blood sampling tube 6 to the slider 11 side may be carried out by moving the second conveying means 9 once to the left side so that a head side of the long blood sampling tube 6 abuts against the second conveying means 9, moving the second conveying means 9 so that the blood sampling tube 6 is transferred stably in an original posture from the intermediate conveyor 8 onto the second conveying means 9, and then moving the second conveying means 9 to the right side. A switch-back movement of the supply conveyor 9 may be determined in consideration, for example, of a dimension in level difference between the intermediate conveyor 8 and the second conveying means 9, the lengths of the blood sampling tubes 6, and a moving speed, for example, of the conveyor 8.

Meanwhile, the blood sampling tubes 6, which are supplied from the conveyor-type first conveying means 7 arranged below the unit of the stockers in a vertical column on the left side, fall to be transferred directly onto the second conveying means 9.

Further, the blood sampling tubes 7, which are dispensed from the blood sampling tube stockers 1 most on the near side, are not conveyed by the conveyor-type first conveying means 7 with partition plates, but dropped and supplied directly onto the intermediate conveyor 8 or the second conveying means 9. Thus, setting is made so that the dispensing is not performed in the case where the blood sampling tube waits at the part corresponding to the slider 11.

The second conveying means 9 conveys the blood sampling tube 6, which is supplied by being dropped, to the right side direction in FIG. 2. A leading end of the blood sampling tube 6 abuts against and presses the arrival detection plate 19 on the terminal end side of the conveyor. With this, the arrival detection plate 19 in the inclined posture is pivoted into a perpendicularly downward posture, and the blood sampling tube 6 is stopped. Note that, at this stop position, an orientation detection sensor (not shown) for the blood sampling tubes 6 detects the cap of the blood sampling tube 6. Based on detection of the cap, it is determined that the blood sampling tube 6 has been conveyed from the cap side, that is, the blood sampling tube 6 has been oriented to the opposite side. Thus, a signal signifying the opposite orientation is output to the printing device 20.

Further, when the arrival detection plate 19 is pressed and urged into the perpendicularly downward posture, arrival detection means such as a light emitting-and-receiving sensor is activated. With this, supply of the blood sampling tube 6 can be detected. In response to this arrival detection signal, the slider 11 that reciprocates in the direction orthogonal to the conveying direction of the second conveying means 9 starts to move. With this, the blood sampling tube 6 that has arrived thereat is pushed out in the horizontal direction so that the blood sampling tube 6 is dropped and supplied to a receiving portion side of the label pasting device 21. In the label pasting device 21, the pressure roller 26 is positioned at a retracted position. When the blood sampling tube 6 is received, the pressure roller 26 advances to press and urge the blood sampling tube 6 to the drive roller 24 side and the support roller 25 side. With this, a driving force of the drive roller 24 is transmitted to the blood sampling tube 6 so that the blood sampling tube 6 rotates in a circumferential direction.

Meanwhile, in the label printing device 20, patient IDs, test items, and necessary items of blood sampling information, such as a type of a blood sampling tube and an amount of blood to be sampled, which are acquired, for example, from the host computer and the computer terminals of doctors, are printed onto the labels paid out from the label roll 22. The contents to be printed are displayed on the touch panel monitor, and an operator can check those contents. As illustrated in FIG. 3, the release sheet of the printed labels is folded back at an acute angle and moved in this state. Thus, only the repulsive labels are fed straight as they are, and naturally released from the release sheet. Then, the label thus released enters a portion between the drive roller 24 and an outer peripheral surface of the blood sampling tube 6, and is taken up and pasted to the outer peripheral surface of the blood sampling tube 6. When the pressure roller 24 is restored by being retracted obliquely downward (left downward in FIG. 3), the blood sampling tube 6, to which the label is pasted, is released from an pasting portion and falls by its own weight to be received into the tray 12.

As described above, preparation of one blood sampling tube of a single type is completed. After that, when blood sampling tubes of other types are requested, the stockers 1 of the corresponding types are driven, and the operation described above is subsequently repeated to receive the blood sampling tubes 6 into the tray 12. When preparation of the blood sampling tubes of all the types requested using the information, for example, from the host computer and the computer terminals of doctors is completed in this way, preparation of blood sampling tubes for blood sampling of one patient is completed. After that, in the same way, blood sampling tubes for other patients may be prepared.

Figure 4:
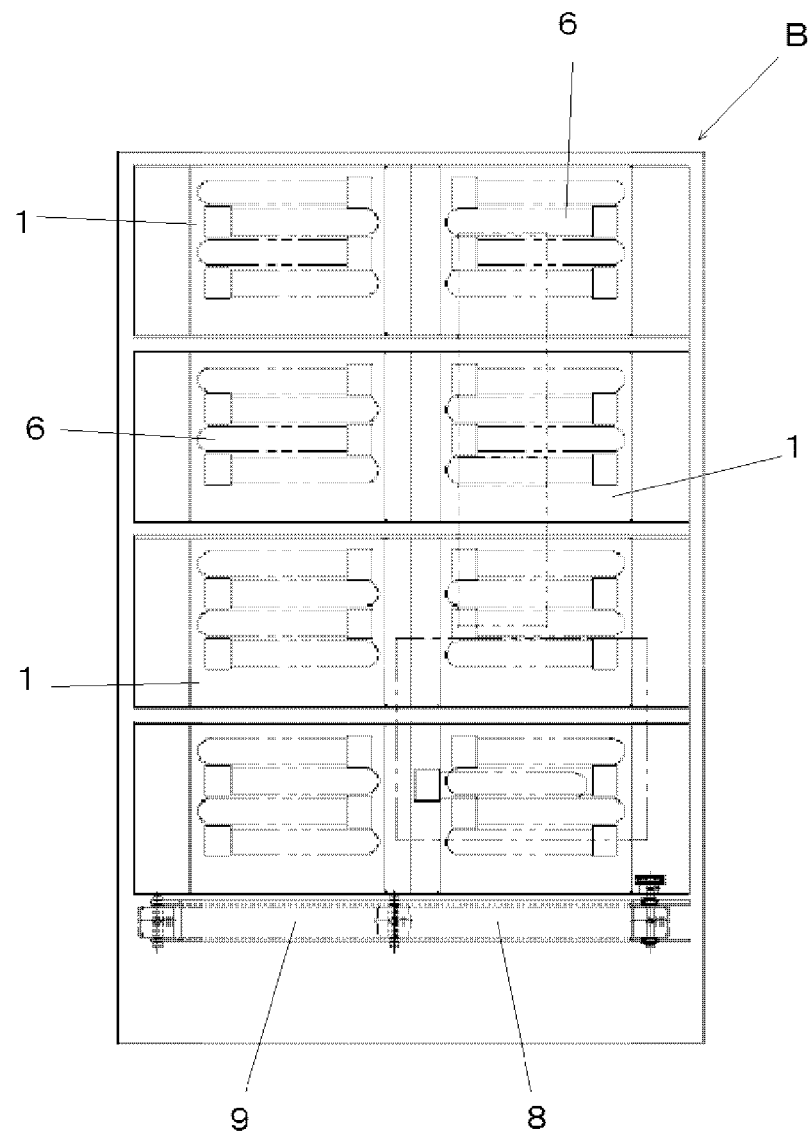
FIG. 4 is an overall plan view of a tube dispenser according to a second embodiment of the present invention.
Figure 5:
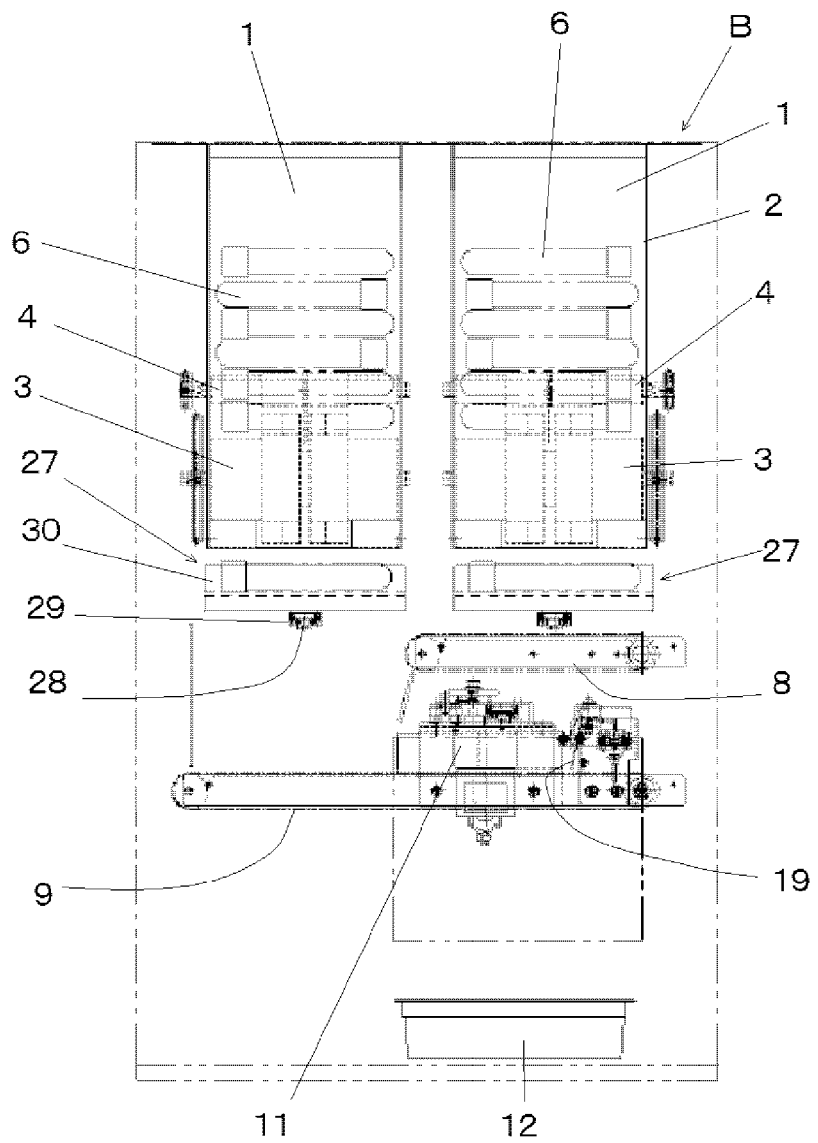
FIG. 5 is an overall front view of the tube dispenser according to the second embodiment of the present invention.
Figure 6:
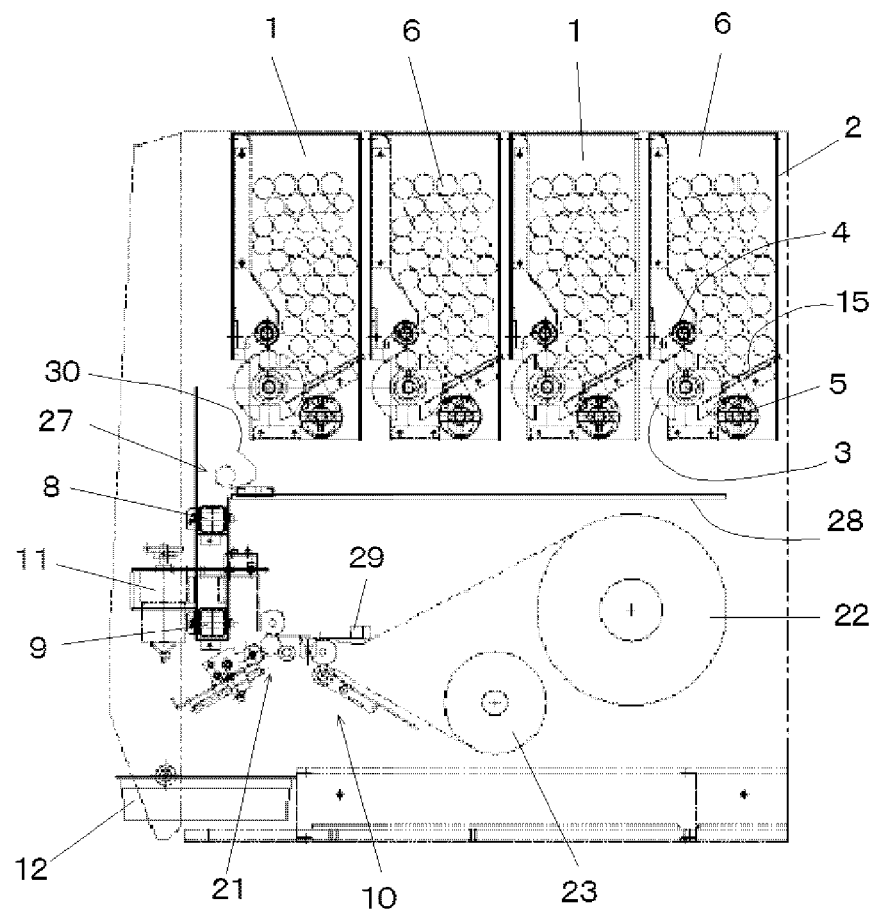
FIG. 6 is a right side view of mechanism portions of the tube dispenser according to the second embodiment of the present invention.

Next, description is made of a second embodiment of the present invention with reference to the plan view of FIG. 4, the front view of FIG. 5, and the left and right side view of FIG. 6. In a double-decker tube dispenser B according to this embodiment, as conveying means for conveying the blood sampling tubes 6 dispensed from the stockers 1 in vertical columns to the intermediate conveyor 8 side or the second conveying means 9 side, bucket-type first conveying means 27 are employed. Other structural features, functions, and advantages are the same as those in the embodiment described above with reference to FIGS. 1 to 3.

As best illustrated in FIGS. 5 and 6, in this embodiment, the bucket-type conveying means 27 arranged below each of the units of the stockers in vertical columns includes a movable member 29 provided over a single rail 28. In side view, an L-shaped support member is mounted in a freely pivotal manner to the movable member 29, and to an upper surface of the support member, a bucket 30 having an inverted V-shape in cross section is mounted while being urged constantly upward by a spring. This spring is stretched between the movable member 29 and the support member. On a terminal end side of the rail 28, a stopper to abut against the support member so as to stop movement thereof is arranged. The bucket 30 is normally directed upward by an urging force of the spring. When the support member abuts against the stopper, the bucket 30 is inclined against the urging force of the spring. With this, the blood sampling tube 6 received in the bucket 30 is dropped and supplied onto the intermediate conveyor 8 or the second conveying means 9. Note that, on a terminal end side of the bucket-type first conveying means 27, a sensor (not shown) for detecting presence or absence of the blood sampling tubes 6 is arranged. With this, in the case where the blood sampling tube waits at the part corresponding to the slider 11, the blood sampling tube 6 is not supplied to the slider 11 side.

Further, the movable member 29 may be moved by a rack-and-pinion system, a belt take-up system, a chain drive system, or a ball screw system.

Based on the information acquired as described above, the control unit determines which type of blood sampling tube is selected, and causes the drive motor 5 to drive the blood sampling tube stocker 1 in which the blood sampling tube 6 of the corresponding type is stocked, the dispensing roll 3 to rotate in a counterclockwise direction in FIG. 6, and the auxiliary roll 4 to rotate in a clockwise direction. In addition, simultaneously, the control unit causes the movable member 29 of the first conveying means 27 to move so that the bucket 30 is positioned below the dispensing roll 3 of the blood sampling tube stocker 1 of the corresponding type and to wait thereat. By driving the dispensing roll 3 and the auxiliary roll 4, the blood sampling tube 6 is fitted and received in the recessed groove 14 of the dispensing roll 3. At this time, even in the case where a cap of the blood sampling tube 6 fitted in the recessed groove 14 adheres to a cap of another blood sampling tube 6, the another blood sampling tube 6 is pushed back by the auxiliary roll 4, and perfectly separated from the blood sampling tube 6 in the recessed groove 14. Then, when the dispensing roll 3 further rotates in the counterclockwise direction, the recessed groove 14 is then directed downward, and the blood sampling tube 6 received therein is dropped by its own weight and supplied into the bucket 30 of the first conveying means 27, which has waited therebelow under the upward state. Then, the blood sampling tube 6 is conveyed by movement of the movable member 29 of the first conveying means 27 to the right side in FIG. 3, and the L-shaped support member stops once immediately before abutting abutment against the stopper, and waits thereat. The sensor on the terminal end side of the conveying means 27 detects this waiting state, and it can be determined that the blood sampling tube 6 has been supplied.

In the case where the blood sampling tube 6 has not waited at the part corresponding to the slider 11 provided on the terminal end side of the second conveying means 9, the bucket-type first conveying means 27 drops and supplies the blood sampling tube 6, which is detected on the terminal end side thereof, onto the intermediate conveyor 8 or the second conveying means 9. The blood sampling tube 6, which is supplied onto the intermediate conveyor 8, is conveyed by the intermediate conveyor 8 to the left side direction in FIG. 5, and then dropped and supplied from the terminal end side thereof onto the second conveying means 9 therebelow.

In the case where the blood sampling tube 6 has waited at the part corresponding to the slider 11, the blood sampling tube 6 is held and caused to wait at this position. Further, the blood sampling tubes 6, which are dispensed from the blood sampling tube stockers 1 most on the near side, are dropped and supplied directly onto the intermediate conveyor 8 or the second conveying means 9. Thus, setting is made so that the dispensing is not performed in the case where the blood sampling tube 6 has waited at the part corresponding to the slider 11.

The second conveying means 9 conveys the blood sampling tube 6, which is supplied by being dropped, to the right side direction in FIG. 5. The leading end of the blood sampling tube 6 abuts against and presses the arrival detection plate 19 on the terminal end side of the conveyor. With this, the arrival detection plate 19 in the inclined posture is pivoted into the perpendicularly downward posture, and the blood sampling tube 6 is stopped. After that, as in the case of the embodiment illustrated in FIGS. 1 to 3, the blood sampling tube 6 is fed to the printing-and-pasting device 10 side, and a printed label is pasted to the blood sampling tube 6. Then, the blood sampling tube 6 is delivered to the tray 12.

Figure 7:
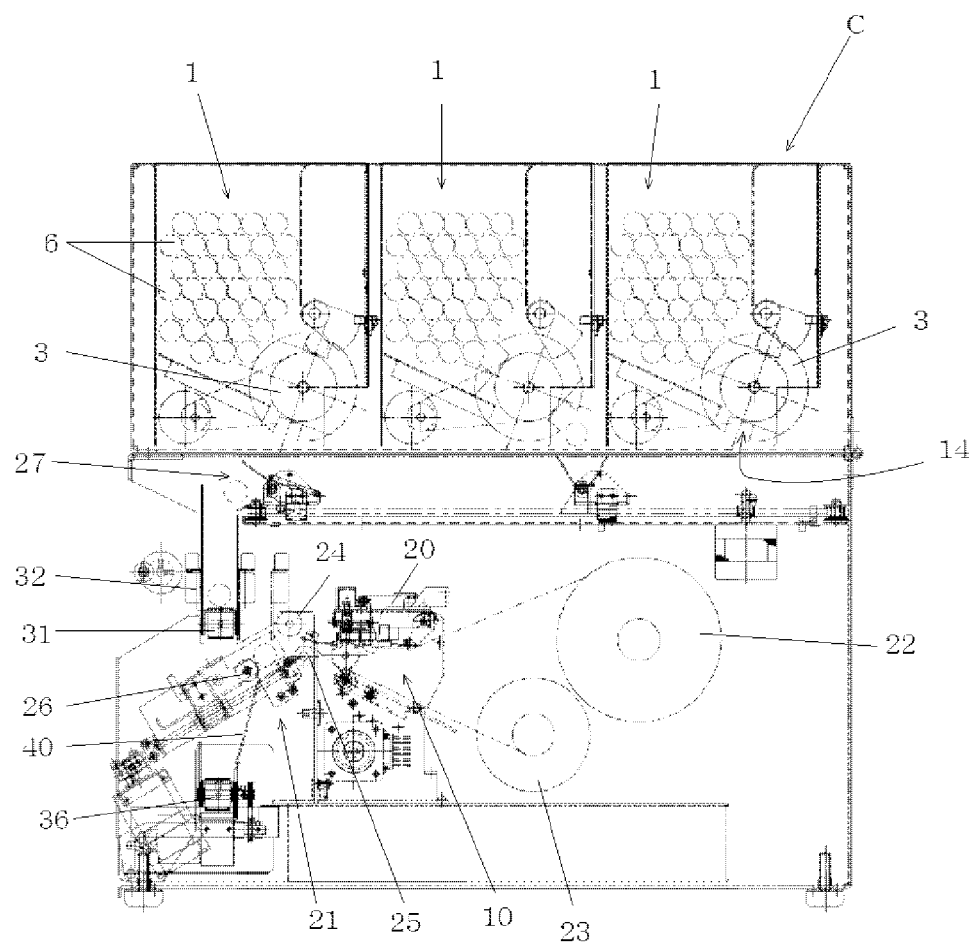
FIG. 7 is a right side view of mechanism portions of a tube dispenser according to a third embodiment of the present invention.
Figure 8:
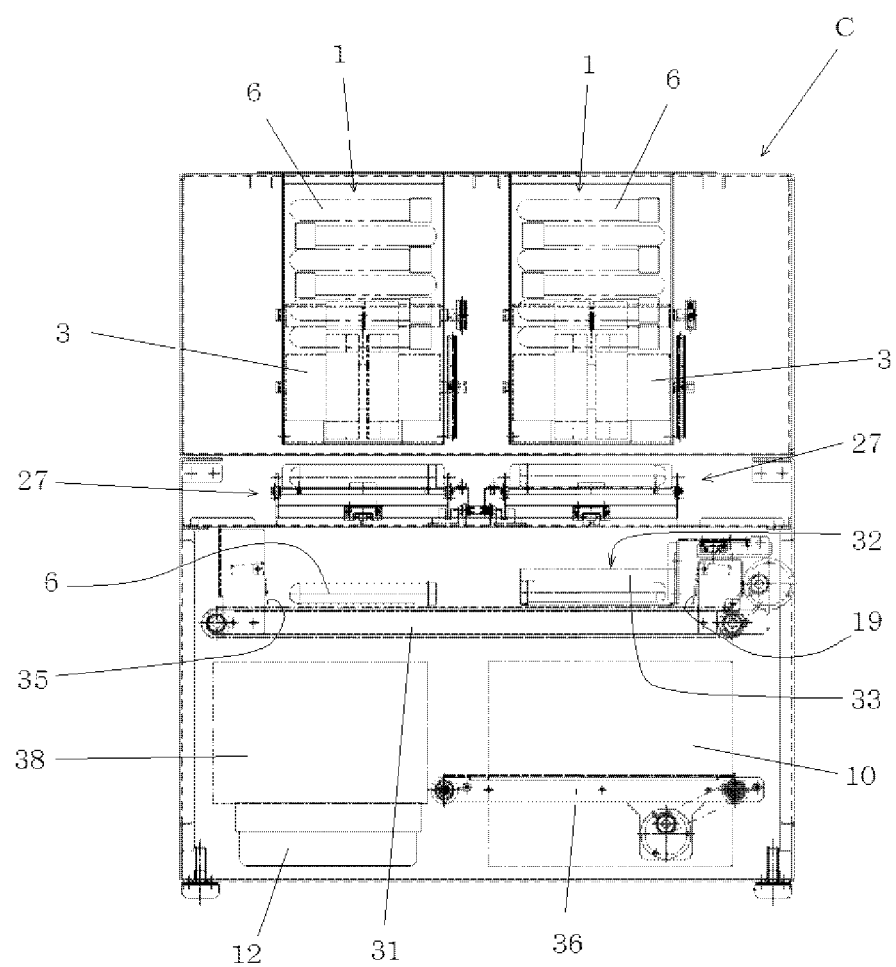
FIG. 8 is a front view of the mechanism portions of the tube dispenser according to the third embodiment of the present invention.
Figure 9:
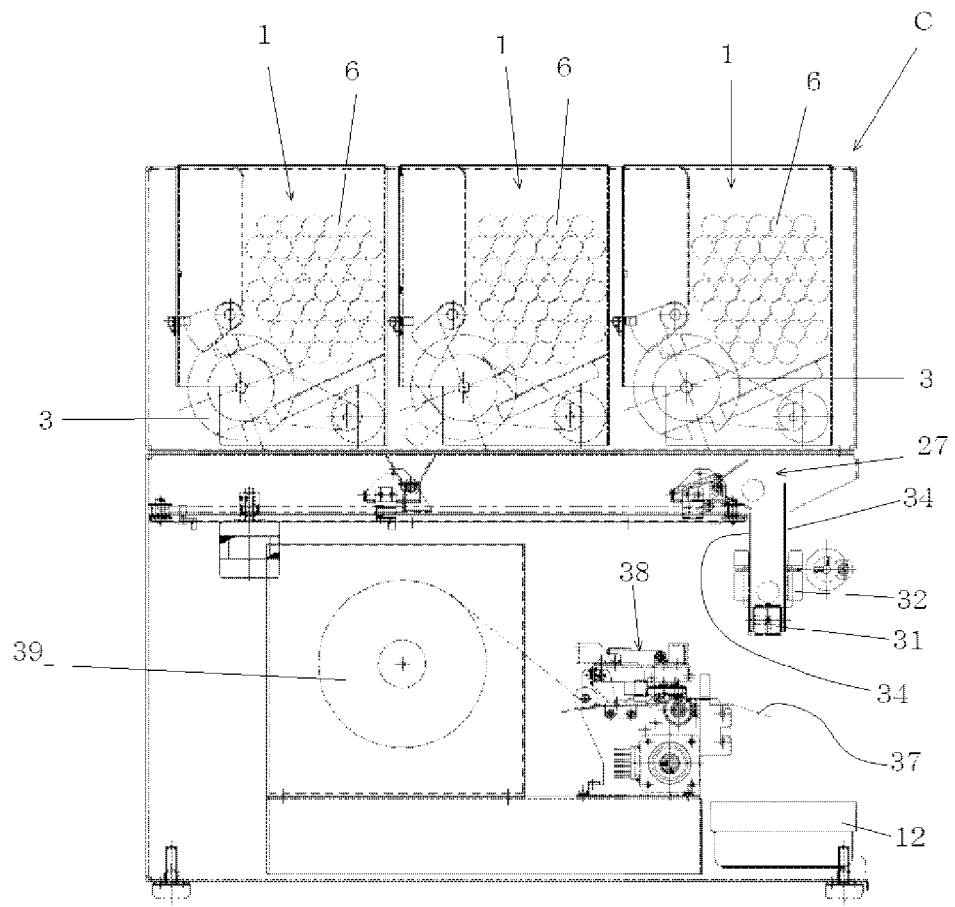
FIG. 9 is a right side view of the mechanism portions of the tube dispenser according to the third embodiment of the present invention.

Next, description is made of a third embodiment of the present invention with reference to FIGS. 7 to 9. In this tube dispenser C, a total of six blood sampling tube stockers 1 are arrayed, specifically, three in vertical columns and two in horizontal rows.

In addition, below each of the vertical columns of the stockers 1, the bucket-type first conveying means 27 for transporting the blood sampling tubes 6 dispensed from the stockers 1 is arranged. The bucket-type first conveying means 27 each have the same structure as those in the case of the second embodiment illustrated in FIGS. 5 and 6. Note that, this embodiment is different from the second embodiment described above in that the dispensing roll 3 of each of the stockers 1 turns in a clockwise direction in FIG. 7 so as to dispense the blood sampling tubes 6 to a depth side (rear portion side) of the apparatus main body.

Further, below the terminal end side of the bucket-type first conveying means 27, in a direction orthogonal thereto, there is provided second conveying means 31 as means for transporting the blood sampling tubes to the printing-and-pasting device 10 side. This second conveying means 31 is arranged so as to cover the two bucket-type first conveying means 27 in a range of from a left end side to a right end side. On a terminal end side of the second conveying means 31 (right side in FIG. 8), there is provided a slider 32 as blood sampling tube transfer means for pushing out and supplying the blood sampling tubes 6 having arrived thereat to the printing-and-pasting means 10. The slider 32 has a C-shape in plan view, and includes, as front and rear side surfaces facing each other, holding plates 33 having height dimensions larger than outer diameter dimensions of the blood sampling tubes 6 placed in a laid posture on the second conveying means 31. In addition, on a lower side in an intermediate portion coupling those holding plates 33 to each other, a space is formed so that the blood sampling tubes 6 can pass therethrough.

Note that, as illustrated in FIGS. 7 and 9, as front and rear side surfaces of the second conveying means 31, guide plates 34 and 34 are provided upright so that the blood sampling tubes 6 dropped and supplied from the bucket-type conveying means 27 onto the supply conveyor 31 do not fall therefrom. In addition, in parts of those guide plates 34 and 34, cutouts are formed correspondingly to the slider 32 so that the slider 32 can reciprocate in the left and right directions in FIGS. 7 and 9.

Meanwhile, orientation detection means for detecting orientations of the blood sampling tubes 6 is provided on a start end side of the second conveying means 31, and the arrival detection means for detecting arrival of the blood sampling tubes 6 is provided on the terminal end side thereof. In the orientation detection means on the start end side, a bottom portion side of the blood sampling tube 6, which passes through a gate (not shown), pivots an L-shaped bottom portion detection plate 35, and light emitted from a light emitting sensor is received. With this, the bottom portion can be identified. When a head portion (cap) side of the blood sampling tube 6 arrives thereat, the cap is engaged with the gate and cannot pass therethrough. With this, the head portion can be identified.

Meanwhile, as in the cases of the first and second embodiments, the arrival detection means on the terminal end side of the second conveying means 31 includes the arrival detection plate 19 having an L-shape. The arrival detection plate 19, which waits in an obliquely inclined posture under a normal state as illustrated in FIG. 8, enters a perpendicularly downward state by being pressed by the blood sampling tubes 6 fed thereto, and simultaneously determines a stop position of the blood sampling tubes 6. Under the inclined waiting state, the arrival detection plate 19 blocks the light emitted from the detection sensor (not shown) such as an infrared sensor and a photo sensor including a light emitting element and a light receiving element, and allows the light emitted from the light emitting element to be received by the light receiving element under the perpendicularly downward state at the time of arrival of the blood sampling tubes 6.

Further, below the second conveying means 31, in front of the printing-and-pasting device 10, a conveyor 36 as means for delivering the blood sampling tubes 6 to which the labels are pasted is arranged in parallel to the second conveying means 31. In addition, on a terminal end side of the delivery conveyor 36, the mounting portion for the tray 12 is provided. In this tray mounting portion, as in the cases of the first and second embodiments described above, the optical sensor (not shown) for detecting presence or absence of the tray 12 is arranged. The sensor may include sensors of a type in which light emitted from a light projecting sensor is detected by a light receiving sensor, and a light emitting-and-receiving sensor of a reflection type.

Yet further, on a depth side with respect to the tray mounting portion, a printing device 38 for labels 37 to be manually pasted is mounted. Patient information and the like are printed on labels paid out from a roll 39 of the labels 37 to be manually pasted, and the labels 37 are cut one by one, and dropped and supplied into the tray 12.

Next, description is made of an operation mode of the tube dispenser C according to the third embodiment, which is structured as described above. The blood sampling tube 6, which is dispensed from any of the stockers 1, is conveyed by the bucket-type first conveying means 27 to the left end side in FIG. 7. Then, the bucket abuts against the stopper. With this, the bucket is inclined, and the blood sampling tube 6 is dropped and supplied onto the second conveying means 31. After the blood sampling tube 6 is supplied, the second conveying means 31 conveys the blood sampling tube 6 to the left direction in FIG. 7. When the blood sampling tube 6 is conveyed from the bottom portion side thereof, the blood sampling tube 6 passes through the gate and pivots the orientation detection plate 35. With this, the light receiving sensor is turned ON. In this way, arrival of the bottom portion can be detected. Meanwhile, when the blood sampling tube 6 is conveyed from the cap side thereof, the cap is engaged with the gate, and the orientation detection plate 35 is not pivoted. In this way, arrival of the cap side can be detected. Detection signals in those cases are transmitted to the label printing device 20 via the control unit, and directions of printing to the labels are determined. Thus, the blood sampling tubes 6 can be randomly loaded regardless of their orientations into the blood sampling tube stockers 1, and hence a burden on an operator can be reduced.

After the orientation of the blood sampling tube 6 is detected in this way, the second conveying means 31 rotates in a reverse direction so that the blood sampling tube 6 is conveyed to the right end direction in FIG. 7. The blood sampling tube 6 enters a center of the C-shaped slider 32. Then, the leading end of the blood sampling tube 6 abuts against and pivots the arrival detection plate 19, and the second conveying means 31 stops being driven. Simultaneously, the slider 32 is moved to the right side in FIG. 7 while holding the blood sampling tube 6. With this, the blood sampling tubes 6 are dropped and supplied to the label pasting device 21. Subsequently, the pressure roller 26 of the label pasting device 21 is moved to the obliquely right-upward direction in FIG. 7 so that the blood sampling tube 6 is pressurized and sandwiched by three rollers of the drive roller 24, the support roller 25, and the pressure roller 26. With this, the blood sampling tube 6 rotates in the circumferential direction. At this time, the label printed with patient information and the like is supplied to a portion between the drive roller 24 and the blood sampling tube 6, and the label is pasted to the blood sampling tube 6.

When pasting of the label is completed, the pressure roller 26 is moved to restore to a release position. Thus, the blood sampling tube 6, to which the label is pasted, is dropped and supplied by its own weight onto the delivery conveyor 36 while being guided by a guide plate 40 (refer to FIG. 7). Then, the delivery conveyor 36 is driven so that the blood sampling tube 6 is transported to the left direction in FIG. 7 and loaded into the tray 12. In this way, the blood sampling tubes 6 of a plurality of types are prepared in accordance with test items for one patient. Further, as for particular blood sampling tubes that are not arranged in any of the six stockers 1, only patient information is printed to labels with the printing device 38 for manual pasting, and the labels are partially cut and loaded into the tray 12. After the preparation of the blood sampling tube 6 and the label to be manually pasted is completed in this way, the tray 12 is taken out, and blood sampling is performed. Note that, at the time of the blood sampling, a hospital staff prepares the particular blood sampling tubes, and the labels to be manually pasted are manually pasted to those tubes by the hospital staff.

INDUSTRIAL APPLICABILITY

By the way, the present invention is not limited to the embodiments described above, and modifications may be made thereto as appropriate. For example, in the tube dispenser, the unit of the stockers in the vertical columns may include a single unit of the stockers in a vertical column, specifically, only a single stocker may be arranged in the horizontal row. In this case, the first conveying means of the conveyor type, the bucket type, and the like for the dispensed blood sampling tubes, which conveys the blood sampling tubes dispensed from the blood sampling tube stockers to the near side, may be arranged below the unit of the stockers in the only one vertical column. The slider as the blood sampling tube transfer means may be arranged below the terminal end side of the first conveying means for the dispensed blood sampling tubes. The label printing device and the label pasting device may be arranged in proximity to the slider. In this way, the tube dispenser including the unit of the stockers in the only one vertical column can be provided, that is, a significantly simple apparatus to be easily introduced even to small hospitals, bloodmobiles, and the like can be provided.

REFERENCE SIGNS LIST

1 . . . blood sampling tube stocker
2 . . . stocker main body
3 . . . dispensing roll
4 . . . auxiliary roll
5 . . . drive roll
6 . . . blood sampling tube
7 . . . conveyor-type first conveying means for dispensed blood sampling tube
8 . . . intermediate conveyor
9 . . . second conveying means for blood sampling tube
10 . . . printing-and-pasting means
11 . . . slider
27 . . . bucket-type first conveying means for dispensed blood sampling tube
28 . . . rail
29 . . . movable member
30 . . . bucket
31 . . . second conveying means for blood sampling tube
32 . . . slider
36 . . . delivery conveyor
38 . . . printing device for label to be manually pasted
A . . . conveyor-type double-decker tube dispenser
B . . . bucket-type double-decker tube dispenser
C . . . double-decker tube dispenser

What is claimed is:

1. A double-decker tube dispenser, comprising:
a plurality of independent blood sampling tube stockers arranged in front to back and side to side so as to define at least two columns and rows of the stockers, for containing blood sampling tubes in a horizontal posture, respectively;
at least two first conveyors, each of which is arranged below the corresponding column of the stockers and extends along the column, configured to convey the blood sampling tubes dispensed from the plurality of independent blood sampling tube stockers of the respective column to a front side of the column;
a second conveyor arranged at one terminal end of the respective first conveyor in a direction orthogonal to the first conveyors configured to receive the blood sampling tubes conveyed by the first conveyors at the terminal end the respective first conveyor, and to transfer the received blood sampling tubes to a position corresponding to a pusher that is provided at a side of the second conveyor, and positioning on a transportation path of the second conveyor;
the pusher configured to push out the blood sampling tubes on the second conveyor in a direction orthogonal to the transportation path of the second conveyor;
and a label printing-and-pasting device arranged in proximity to the pusher and configured to receive the blood sampling tube pushed out, wherein the label printing-and-pasting device is positioned below one of the columns.

2. The double-decker tube dispenser according to claim 1, further comprising:
an orientation detector configured to detect orientation of the blood sampling tubes, which is arranged on one end of the second conveyor; and
arrival detector arranged on another end of the second conveyor,
wherein the pusher is arranged on the another end of the second conveyor.

3. The double-decker tube dispenser according to claim 1, further comprising a blood sampling tube delivery conveyor arranged below and parallel to the second conveyor.

4. The double-decker tube dispenser according to claim 1, further comprising a printer arranged below another one of the columns of the plurality of independent blood sampling tube stockers, for printing labels to be manually pasted.

5. The double-decker tube dispenser according to claim 1, further comprising an intermediate conveyor provided between at least one of the first conveyor and the second conveyor,
wherein the blood sampling tubes conveyed by said first conveyor are fed to the second conveyor through of the intermediate conveyor.

6. The double-decker tube dispenser according to claim 1, wherein the columns of the plurality of independent blood sampling tube stockers comprise two columns wherein a width dimension of an entire apparatus is set to be larger than a total width dimension of the two columns of independent blood sampling tube stockers in the horizontal direction by an amount corresponding to a dimension of a casing.

* * * * *